United States Patent [19]

Kozar

[11] Patent Number: 5,456,508
[45] Date of Patent: Oct. 10, 1995

[54] CONTACT LENS SUCTION CUP

[76] Inventor: John J. Kozar, 800 Carl Ave., New Kensington, Pa. 15068

[21] Appl. No.: 257,128

[22] Filed: Jun. 9, 1994

[51] Int. Cl.$^6$ ............................................. A61F 9/00
[52] U.S. Cl. ............................................. 294/1.2; 294/64.1
[58] Field of Search ..................................... 294/1.2, 64.1; 606/107; 206/5.1

[56] References Cited

U.S. PATENT DOCUMENTS

| | | | |
|---|---|---|---|
| 3,129,971 | 4/1964 | Kobler | 294/64 |
| 3,424,486 | 1/1969 | Corley | 294/1.2 |
| 3,879,076 | 4/1975 | Barnett | 294/1 CA |
| 3,897,968 | 8/1975 | Allen, Jr. | 294/1 CA |
| 4,079,976 | 3/1978 | Rainin et al. | 294/1.2 |
| 4,123,098 | 10/1978 | Shoup | 294/1.2 |
| 4,164,099 | 8/1979 | Grant | 294/1.2 X |
| 4,326,742 | 4/1982 | Ingram | 294/1 CA |
| 4,332,408 | 6/1982 | Cointment | 294/1.2 |
| 4,378,126 | 3/1983 | Procenko | 294/1 CA |
| 5,050,918 | 9/1991 | Kolze | 294/1.2 |

*Primary Examiner*—Dean Kramer
*Attorney, Agent, or Firm*—Jacobson, Price, Holman & Stern

[57] ABSTRACT

A concave surface for engaging and conforming to the convex side of a contact lens is provided together with partial vacuum generating structure operative to generate a slight degenerative partial vacuum at the concave surface to allow a pick up device upon which the concave surface is defined to be used to momentarily pick up and move a contact lens into close proximity to the cornea of an eye to which the contact lens is to be applied.

10 Claims, 1 Drawing Sheet

U.S. Patent     Oct. 10, 1995     5,456,508
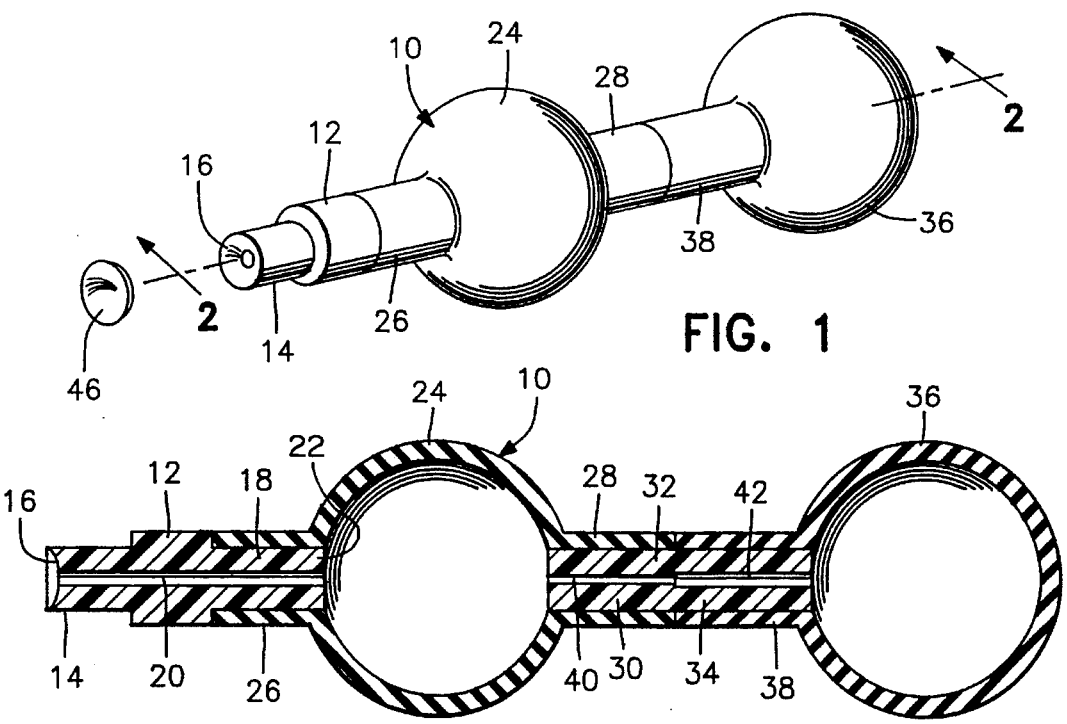
FIG. 1
FIG. 2
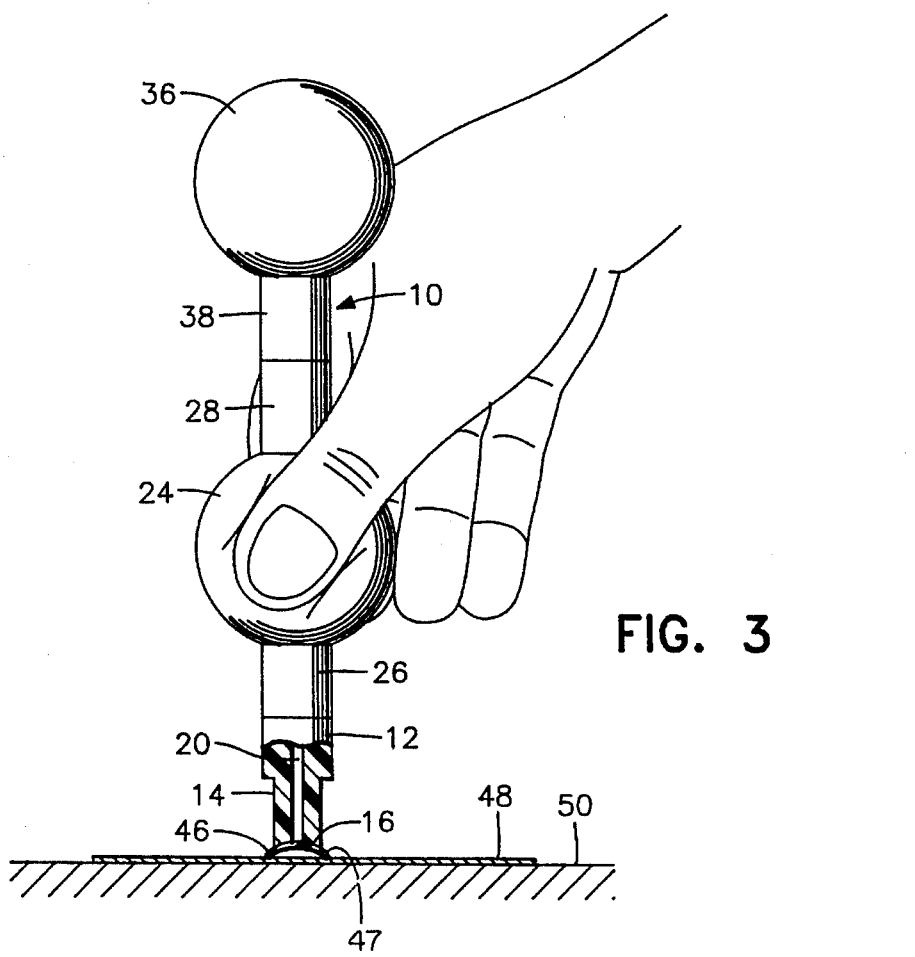
FIG. 3

5,456,508

CONTACT LENS SUCTION CUP

BACKGROUND OF THE INVENTION

1. Field of the Invention

This invention relates to a suction cup pick up and support for a contact lens with the support including structure for generating a degenerative slight partial vacuum at a concave lens pick up surface.

2. Description of Related Art

Various different forms of vacuum pick up and applying devices for contact lenses heretofore have been provided. Examples of these previously known devices are disclosed in U.S. Pat. Nos. 3,129,971, 3,879,076, 3,897,968, 4,326,742, 4,378,126 and 5,050,918. However, these previously known forms of contact lens pick up and applicator devices require actuation techniques which must be learned and which require reasonable dexterity.

SUMMARY OF THE INVENTION

The contact lens suction cup of the instant invention is designed primarily for picking up contact lenses, supporting a contact lens while a few drops of saline solution are deposited therein and for thereafter applying a contact lens to a user's cornea.

The suction cup, as denoted by its name, is operable to generate a slight partial vacuum (at a concave surface adapted to conform to the convex side of a contact lens) and with the slight partial vacuum generated being rapidly degenerative. Further, the suction cup comprising the apparatus of the instant invention is constructed in a manner such that it may be manipulated between the thumb and forefinger of a user's hand not only to generate the desired slight partial vacuum to pick up a contact lens, but also to rapidly thereafter move the supported contact lens into close proximity with the associated cornea, all without changing a thumb and forefinger grip of the user's hand on the suction cup.

The main object of this invention is to provide a contact lens pick up and handling device which may be readily utilized to pick up a contact lens and rapidly position the contact lens in close proximity to the associated user's cornea.

Another object of this invention is to provide a suction cup pick up for a contact lens in accordance with the preceding object and wherein the suction or partial vacuum generated at the concave lens pick up surface of the suction cup is of the rapidly degenerative type, whereby the partial vacuum generated to pick up an associated contact lens will degenerate within approximately two seconds to thereby allow the user of the suction cup to rapidly position the supported contact lens in close proximity to the associated eye cornea and to thereafter place a contact lens into position against the cornea, the surface tension and capillary attraction between the cornea and the inserted contact lens being sufficient to overcome the considerably less pronounced surface tension and capillary attraction tending to maintain the contact lens in engagement with the suction cup.

A further important object of this invention is to provide a contact lens pick up and applying suction cup constructed in a manner whereby proficient usage thereof may be quickly learned.

Yet another object of this invention is to provide a device in accordance with the preceding objects which is particularly well adapted to be utilized by persons with arthritic hands or prosthetic arm extremities.

A further important object of this invention is to provide a device in accordance with the preceding objects which tends to be maintained more sterile throughout repeated usage thereof.

A final object of this invention to be specifically enumerated herein is to provide a contact lens suction cup for picking up and inserting contact lenses and which will conform to conventional forms of manufacture, be of simple construction and easy to use so as to provide a device that will be economically feasible, long lasting and relatively trouble free in operation.

These together with other objects and advantages which will become subsequent apparent reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

FIG. 1 is a perspective view of the contact lens suction cup of the instant invention;

FIG. 2 is a slightly enlarged longitudinal vertical sectional view taken substantially upon the plain indicated by the section line 2—2 of FIG. 1; and FIG. 3 is a side elevational view of the contact lens suction cup in the process of being used to pick up a wetted contact lens from a wetted tissue paper.

DESCRIPTION OF THE PREFERRED EMBODIMENT

Referring now more specifically to the drawings the numeral 10 generally designates the contact lens suction cup of the instant invention. The suction cup 10 includes an elongated lens applicator 12 constructed of "NYLON" or the like and including a first diametrically reduced end portion 14 having a partial concave spherical end face 16. The lens applicator 12 also includes a second diametrically reduced remote end portion 18 and a longitudinal duct 20 extends through the lens applicator 12 with one end of the duct 20 opening centrally through the surface 16 and the other end opening outwardly through the end surface 22 opposite the end surface 16. A hollow squeeze bulb 24 constructed of rubber includes a first tubular neck 26 and the neck 26 is tightly and sealingly telescoped over the end portion 18. The squeeze bulb 24 also includes a second tubular neck 28 opening outwardly from the squeeze bulb 24 in a direction remote from the direction in which the tubular neck opens outwardly of the squeeze bulb 24 and an elongated tubular fitting having remote ends 32 and 34 has its end 32 snugly telescoped within the tubular nipple 38.

A second squeeze bulb or reservoir 36 is provided and includes a single tubular neck 38 snugly telescoped over the end 34 of the tubular fitting 30. The squeeze bulb 36 is constructed of rubber and the tubular fitting 30 is constructed of a suitable shape retentive plastic such as "NYLON".

From FIG. 2 of the drawings it may be seen that the end 32 has a small diameter central longitudinal bore or vacuum degenerating bleed passage section 40 formed therethrough and that the end portion 34 includes a central longitudinal passage section 42 formed therethrough with which the passage section 40 is communicated.

In operation, the lens handling device has the squeeze bulb 24 thereof gripped between the thumb and forefinger of the user's hand 44, in somewhat the manner in which a pencil or pen is held, and the device 10 is held in a vertical position with its end surface 16 disposed lowermost. Thereafter, the squeeze bulb 24 may be slightly squeezed and the device 10 may be lowered downwardly into contact with a moistened contact lens 46 disposed on a piece of moistened tissue paper 48 or the like. When the device 10 is engaged with the contact lens 46, the end surface 16 is engaged with and generally conforms to the contour of the convex outer surface 47 of the lens 46. Accordingly, when the manual pressure squeezing the squeeze bulb 24 is released, the air pressure within the duct 20 is reduced so that when the device 10 is thereafter lifted away from the tissue paper 48 disposed on the surface 50 the greater air pressure below the central portion of the contact lens 46 will maintain the lens 46 in contact with the end surface 16. The device can then may be inverted to a position with the end surface 16 and lens 46 supported therefrom disposed uppermost and moved into position with the contact lens 46 closely opposing the user's eye to which the lens 46 is to be applied.

The time period involved in lifting the contact lens 46 from the tissue paper 48, inverting the device 10 and positioning the latter with the contact lens closely opposing the user's eyeball after release of squeezing pressure on the squeeze bulb 24, takes approximately one to two seconds.

From the instant the squeezing pressure on the squeeze bulb 24 is released, the partial vacuum within the interior of the squeeze bulb 24 and the duct 20 is gradually decreased or degenerating as a result of some of the air within the squeeze bulb or reservoir 36 and the passage sections 40 and 42 being slowly admitted into the interior of the squeeze bulb 24 and the duct 20 through the restricted flow bleed passage section 40. Accordingly, by the time the device 10 is inverted and positioned with the contact lens 46 closely opposing the eye to which the contact lens 46 is to be applied, the partial vacuum within the squeeze bulb 24 and the duct 20 has been appreciably lessened.

Thereafter, as the concave side of the contact lens 46 is applied to the user's eye, the moistened surfaces of the eye and the contact lens 46 exclude all of the air between the eye and the contact lens 46 such that when the device 10 is then moved away from the eye the air pressure on that portion of the contact lens 46 outwardly of the end face 16 and the attraction of the lens to the cornea of the eye that occurs due to fluid attraction characteristics will allow the lens 46 to be easily disengaged from the end surface 16 and remain in place upon the user's cornea.

Although FIG. 3 illustrates the device 10 as being held in generally the same manner in which a pencil is held, if it is desired, the device 10 may be held in generally the same manner in which a pointer is held (with the squeeze bulb 24 held between the thumb and forefinger but with the squeeze bulb 36 on the palm side of the hand 44). This manner of gripping the device 10 may be helpful to arthritic persons and provide a more comfortable positioning of the device 10 immediately prior to application of the contact lens 46 to the user's cornea.

It is also pointed out that if the squeeze bulb 24 is squeezed slightly too much, it merely takes a little longer time for the partial vacuum within the squeeze bulb 24 and the duct 20 to be reduced sufficient to enable the end surfaces 16 to release from the contact lens 46 after the latter has been applied to the user's cornea.

The foregoing is considered as illustrative only of the principles of the invention. Further, since numerous modifications and changes readily will occur to those skilled in the art, it is not desired to limit the invention to the exact construction and operation shown and described, and, accordingly, all suitable modifications and equivalents may be resorted to, falling within the scope of the invention.

What is claimed is as follows:

1. A contact lens handling device including an elongated lens applicator having a first end portion provided with a concave surface for engaging the convex side of a contact lens, a second remote end portion and at least one duct having a first end opening centrally through said concave surface and a second end opening outwardly of said second end portion, a hollow squeeze bulb provided with a first tubular neck opening thereinto, said first tubular neck being telescoped over said second end portion and communicating said second end with the interior of said squeeze bulb, said squeeze bulb including a second tubular neck opening thereinto, an elongated tubular fitting having remote ends and defining a passage formed longitudinally therethrough, one of said remote ends being telescoped into said second tubular neck, a hollow reservoir including an outwardly opening neck, the last mentioned neck being disposed in telescopic engagement with the other of said remote ends, at least one portion of said passage being considerably restricted in cross sectional area as compared to the cross sectional area of said duct.

2. The device of claim 1 wherein said last mentioned neck is telescoped over said other of said remote ends.

3. The device of claim 1 wherein said squeeze bulb is constructed of shape retentive deformable resilient material.

4. The device of claim 3 wherein said first end portion is constructed of shape retentive material.

5. The device of claim 4 wherein said reservoir comprises a second squeeze bulb.

6. A contact lens handling device including a lens applicator having a first portion provided with a concave surface for engaging the convex side of a contact lens, a second remote portion and at least one duct having a first end opening through said concave surface and a second end opening outwardly of said second portion, a hollow partial vacuum chamber with which said second end is sealingly communicated and adapted to have a slight partial vacuum generated therein, a closed hollow reservoir, and restricted air flow bleed passage means communicating the interior of said reservoir with the interior of said vacuum chamber, said restricted air flow bleed passage means being more restrictive to the flow of air therethrough than said one duct.

7. The device of claim 6 wherein the interior volume of said partial vacuum chamber is generally equal to the interior volume of said reservoir.

8. The device of claim 7 wherein said partial vacuum chamber comprises the interior of a squeeze bulb.

9. In combination with a wetted contact lens having a convex outer surface, a contact lens handling device including a manually manipulative lens applicator defining a concave surface sealingly engaging the wetted convex outer surface of said contact lens in fluid tight relation therewith, and manually actuable partial vacuum generating means operative to generate a partial vacuum at said concave surface on said convex outer surface, said partial vacuum generating means including vacuum degenerating means operative, subsequent to actuation of said partial vacuum generating means to generate said partial vacuum, to automatically rapidly degenerate partial vacuum independent of further manual actuation of said partial vacuum generating means.

10. The device of claim 9 wherein said partial vacuum degenerating means defines a closed hollow reservoir in restricted air flow communication with said concave surface.

* * * * *